(12) United States Patent
Suzuki et al.

(10) Patent No.: US 10,488,357 B2
(45) Date of Patent: Nov. 26, 2019

(54) ELECTRIC CONDUCTIVITY METER

(71) Applicant: HORIBA Advanced Techno, Co., Ltd., Kyoto-shi, Kyoto (JP)

(72) Inventors: Riichiro Suzuki, Kyoto (JP); Hidekazu Takahashi, Kyoto (JP); Kentaro Inoue, Kyoto (JP); Hiroko Kizaki, Kyoto (JP)

(73) Assignee: HORIBA ADVANCED TECHNO, CO., LTD., Kyoto (JP)

( * ) Notice: Subject to any disclaimer, the term of this patent is extended or adjusted under 35 U.S.C. 154(b) by 238 days.

(21) Appl. No.: 15/794,340

(22) Filed: Oct. 26, 2017

(65) Prior Publication Data

US 2018/0120247 A1    May 3, 2018

(30) Foreign Application Priority Data

Nov. 1, 2016  (JP) ................................. 2016-214410

(51) Int. Cl.
| | | |
|---|---|---|
| *G01N 27/08* | (2006.01) | |
| *G01R 27/22* | (2006.01) | |
| *G01N 27/06* | (2006.01) | |
| *G01R 31/12* | (2006.01) | |
| *G01N 27/04* | (2006.01) | |

(52) U.S. Cl.
CPC ............ *G01N 27/08* (2013.01); *G01R 27/22* (2013.01); *G01N 27/04* (2013.01); *G01N 27/06* (2013.01); *G01R 31/1263* (2013.01)

(58) Field of Classification Search
CPC ........ G01R 27/00; G01R 27/02; G01R 27/08; G01R 27/14; G01R 27/20; G01R 27/22; G01R 31/00; G01R 31/12; G01N 27/00; G01N 27/02; G01N 27/04; G01N 27/06; G01N 27/08
USPC .......................... 324/600, 649, 691, 693, 701
See application file for complete search history.

(56) References Cited

U.S. PATENT DOCUMENTS

| | | | | |
|---|---|---|---|---|
| 3,614,489 A | * | 10/1971 | Jensen .................... | H02K 44/10 310/11 |
| 3,928,164 A | * | 12/1975 | Shepard, Jr. .............. | C25B 9/16 204/260 |
| 4,059,498 A | * | 11/1977 | Crissman ............... | B01D 35/06 204/562 |
| 4,063,153 A | * | 12/1977 | Dechene .............. | G01N 27/226 324/434 |
| 4,101,827 A | * | 7/1978 | Offner ..................... | G01M 3/18 324/559 |

(Continued)

FOREIGN PATENT DOCUMENTS

JP          10-132775          5/1998

*Primary Examiner* — Hoai-An D. Nguyen
(74) *Attorney, Agent, or Firm* — Greenblum & Bernstein, P.L.C.

(57) ABSTRACT

In order to avoid an electrode from disturbing a flow of a fluid in a flow channel in case that the electrode of an electric conductivity meter is arranged in the flow channel, the electric conductivity meter comprises two tubular electrodes inside of each of which respectively formed is an inner flow channel where the fluid flows, and an electrode holder that communicates each of the inner flow channels of the two electrodes and that holds the two electrodes. The electrode holder holds the two electrodes by making an engagement with each outer peripheral surface of mutually facing axial direction end parts of the two electrodes.

8 Claims, 8 Drawing Sheets

(56) References Cited

U.S. PATENT DOCUMENTS

| | | | | |
|---|---|---|---|---|
| 5,008,628 A * | 4/1991 | Krigmont | ............ | G01N 27/043 |
| | | | | 324/464 |
| 5,416,425 A * | 5/1995 | Mouaici | ................ | G01N 27/07 |
| | | | | 324/690 |
| 6,281,689 B1 * | 8/2001 | Chase | ................ | D21G 9/0009 |
| | | | | 324/691 |
| 6,441,625 B1 * | 8/2002 | McAllister | ........... | G01N 27/226 |
| | | | | 324/226 |
| 8,264,241 B2 * | 9/2012 | Slezak | ................ | G01N 27/226 |
| | | | | 324/658 |
| 8,525,534 B2 * | 9/2013 | Brandt | .................... | G01F 1/74 |
| | | | | 324/694 |
| 2010/0147700 A1 * | 6/2010 | Field | ................ | A47L 11/4083 |
| | | | | 205/687 |
| 2010/0292944 A1 * | 11/2010 | Howell | ................ | G01N 27/08 |
| | | | | 702/65 |
| 2018/0246050 A1 * | 8/2018 | Momose | ................ | G01N 27/08 |

\* cited by examiner

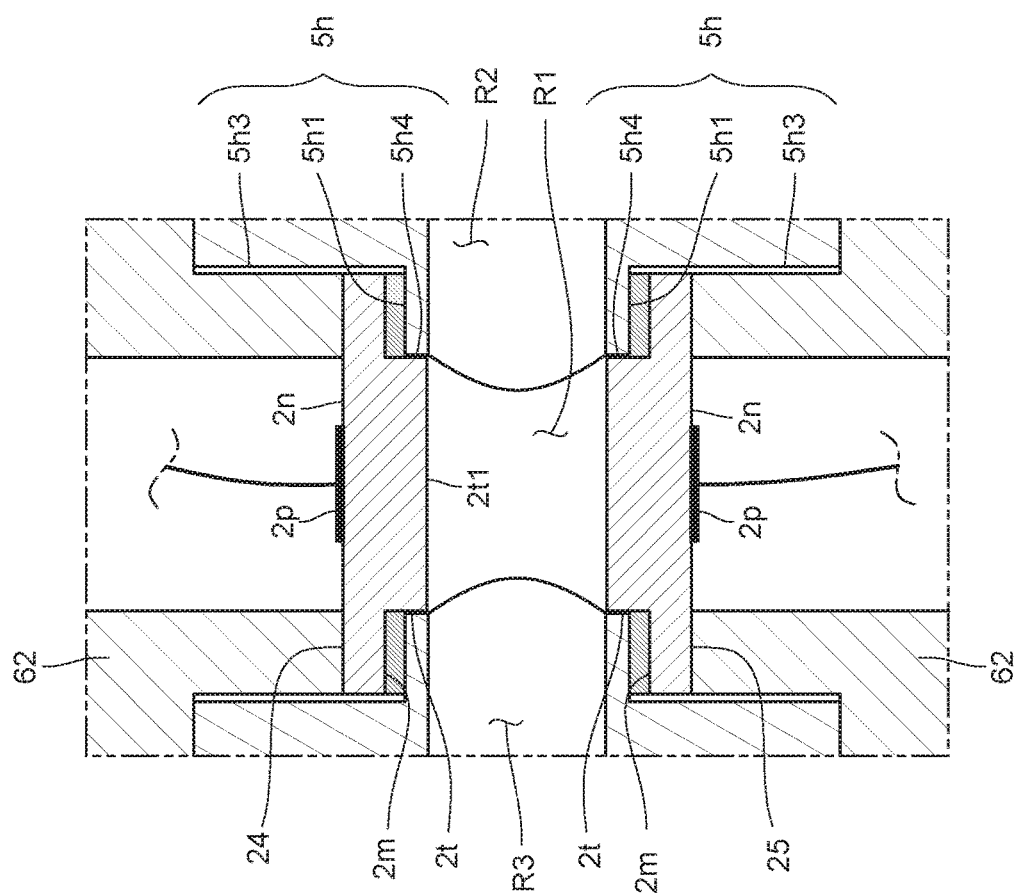

ELECTRIC CONDUCTIVITY METER

FIELD OF THE ART

This invention relates to an electric conductivity meter that measures electric conductivity of a liquid sample between at least two electrodes.

BACKGROUND ART

For example, an electric conductivity meter that measures electric conductivity of a chemical liquid is used in order to control concentration used for, for example, a semiconductor manufacturing process.

The electric conductivity meter comprises, as shown in the patent document 1, a pair of bar-shaped electrodes and an electrode support member that supports a pair of the above-mentioned electrodes, and is so configured that a pair of the electrodes project in a flow channel where a fluid such as a chemical liquid flows as to make a pair of the electrodes contact with the fluid.

PRIOR ART DOCUMENT

Patent document 1 Japanese Unexamined Patent Application Publication No. 10-132775

DISCLOSURE OF THE INVENTION

Problems to be Solved by the Invention

However, in case of measuring concentration of slurry used for chemical mechanical polishing (CMP) in a semiconductor manufacturing process or the like, a pair of the electrodes that project in the flow channel prevent the flow of the slurry so that the slurry might reside on a pair of the electrodes or in a liquid stagnation around the electrodes and adhere to the electrodes. The slurry that adheres to the electrodes is not only a cause of a measurement error but also requiring the flow channel be washed frequently.

Then the present claimed invention intends to solve all of the above-mentioned problems and a main object of this invention is to avoid the electrodes from disturbing the flow of the fluid in case of providing the electrode of the electric conductivity meter in the flow channel.

Means to Solve the Problems

More specifically, the electric conductivity meter in accordance with this invention is an electric conductivity meter that measures electric conductivity of a fluid and that comprises at least two tubular electrodes inside of each of which respectively formed is an inner flow channel where the fluid flows, and an electrode holder that communicates each of the inner flow channels of the above-mentioned at least two electrodes and that holds the above-mentioned at least two electrodes, and is characterized by that the electrode holder holds the above-mentioned at least two electrodes by making an engagement with each outer peripheral surface of mutually facing axial direction end parts of the above-mentioned at least two electrodes.

In accordance with this arrangement, unlike a conventional arrangement wherein the electrode projects in the flow channel, since the flow channel where the fluid flows is formed by the two tubular electrodes, the flow of the fluid is difficult to be disturbed by the electrode. With this arrangement, even though the fluid is slurry, it is possible to reduce a possibility that the slurry resides on the electrodes or in liquid stagnation space around the electrodes. In addition, it is also possible both to improve assemblability and to communalize components by holding two electrodes by the common electrode holder.

It is preferable that the electrode holder comprises a spacer part that locates between the mutually facing axial direction end parts and two tubular parts each of which surrounds each of the outer peripheral surfaces of the mutually facing axial direction end parts.

In accordance with this arrangement, In addition, since the distance between the two electrodes is specified by the spacer part of the electrode holder and the center axis of each electrode is positioned by the two cylindrical parts, it is possible to improve the measurement accuracy. In addition, since the cylindrical part surrounds the outer peripheral surface of the mutually facing axial direction end part, it is possible to secure engagement of the electrode with the electrode holder.

In order to prevent solid particles contained in the fluid from residing between two electrodes, it is preferable that the spacer part is formed over the entire circumferential direction of the mutually facing axial direction end parts, and an inner peripheral surface of the spacer part and an inner peripheral surface of the electrodes locate on approximately the same plane. To locate on generally the same surface means that the inner peripheral surface of the spacer part locates on the same surface as the inner peripheral surface of the electrode to an extent that no solid particle resides or to an extent that the measurement error can be ignored even though the solid particles reside.

In order to give corrosion resistance to the fluid, it is preferable that the above-mentioned at least two electrodes are made of carbon.

As a concrete embodiment of the electric conductivity meter conceived is the electric conductivity meter that further comprises a housing block that houses the above-mentioned at least two electrodes and the electrode holder and that has an introducing path to introduce the fluid and a discharging path to discharge the fluid. With this arrangement, in order to facilitate positioning of the two electrodes to the housing block, it is preferable that the electrode holder is positioned to the housing block, and the inner flow channel communicates with the introducing path and the discharging path.

In addition, the electric conductivity meter in accordance with this invention is the electric conductivity meter that has an electrode arranged to make contact with a fluid flowing in a flow channel, and is characterized by that a flow channel block inside of which formed is the flow channel is comprised, the flow channel block has a through bore that is in communication with the flow channel and where the electrode is arranged, an inner surface of the through bore has an engaging part with which the flow channel side end surface of the electrode makes an engagement and an expanding part that expands toward the flow channel side at the flow channel side of the engaging part.

In accordance with this arrangement, since the inner surface of the through bore where the electrode is arranged has the expanding part that expands toward the flow channel side at the flow channel side of the engaging part with which the electrode engages, it is possible to reduce space where the fluid resides as being space formed in front of the flow channel side end surface of the electrode, and to hardly intercept smooth flow of the fluid. With this arrangement, even though the fluid is the slurry, it is possible to reduce a possibility that the slurry resides on the electrodes or in liquid stagnation space around the electrodes.

Furthermore, the electric conductivity meter in accordance with this invention is the electric conductivity meter that has an electrode arranged to make contact with a fluid flowing in a flow channel, and is characterized by that a flow channel block inside of which formed is the flow channel is comprised, the flow channel block has a through bore that is in communication with the flow channel and where the electrode is arranged, an inner surface of the through bore has an engaging part with which the flow channel side end surface of the electrode makes an engagement, and the electrode has a projecting part that projects toward the flow channel side more than the engaging part.

In accordance with this arrangement, since the inner surface of the through bore where the electrode is arranged has the engaging part with which the electrode makes an engagement and the electrode has the projecting part that projects toward the flow channel side more than the engaging part, it is possible to reduce space where the fluid resides as being space formed in front of the flow channel side end surface of the electrode, and to hardly intercept smooth flow of the fluid. With this arrangement, even though the fluid is slurry, it is possible to reduce a possibility that the slurry resides on the electrodes or in liquid stagnation space around the electrodes.

Effect of the Invention

In accordance with the arrangement of this invention, it is possible to avoid the electrodes from disturbing the flow of the fluid. With this arrangement, it is possible to make the solid particles contained in the fluid not likely reside on the electrodes or around the electrodes.

BRIEF DESCRIPTION OF THE DRAWINGS

FIG. 8 is an enlarged cross-sectional view showing a configuration near a through bore.

BEST MODES OF EMBODYING THE INVENTION

First Embodiment

An electric conductivity meter 100 of a first embodiment in accordance with this invention will be explained with reference to drawings.

The electric conductivity meter 100 in accordance with the first embodiment is used for measuring concentration of a fluid (hereinafter called as a liquid sample) such as silica-based or ceria-based slurry that is used for chemical mechanical polishing (CMP) in a semiconductor manufacturing process, and calculates electric conductivity (S/m (Siemens/meter)) of the liquid sample by measuring the electric conductivity of the liquid sample between at least two electrodes. The electric conductivity meter 100 can be also used for measuring concentration of a chemical liquid other than CMP used in a semiconductor manufacturing process.

Figure 1:
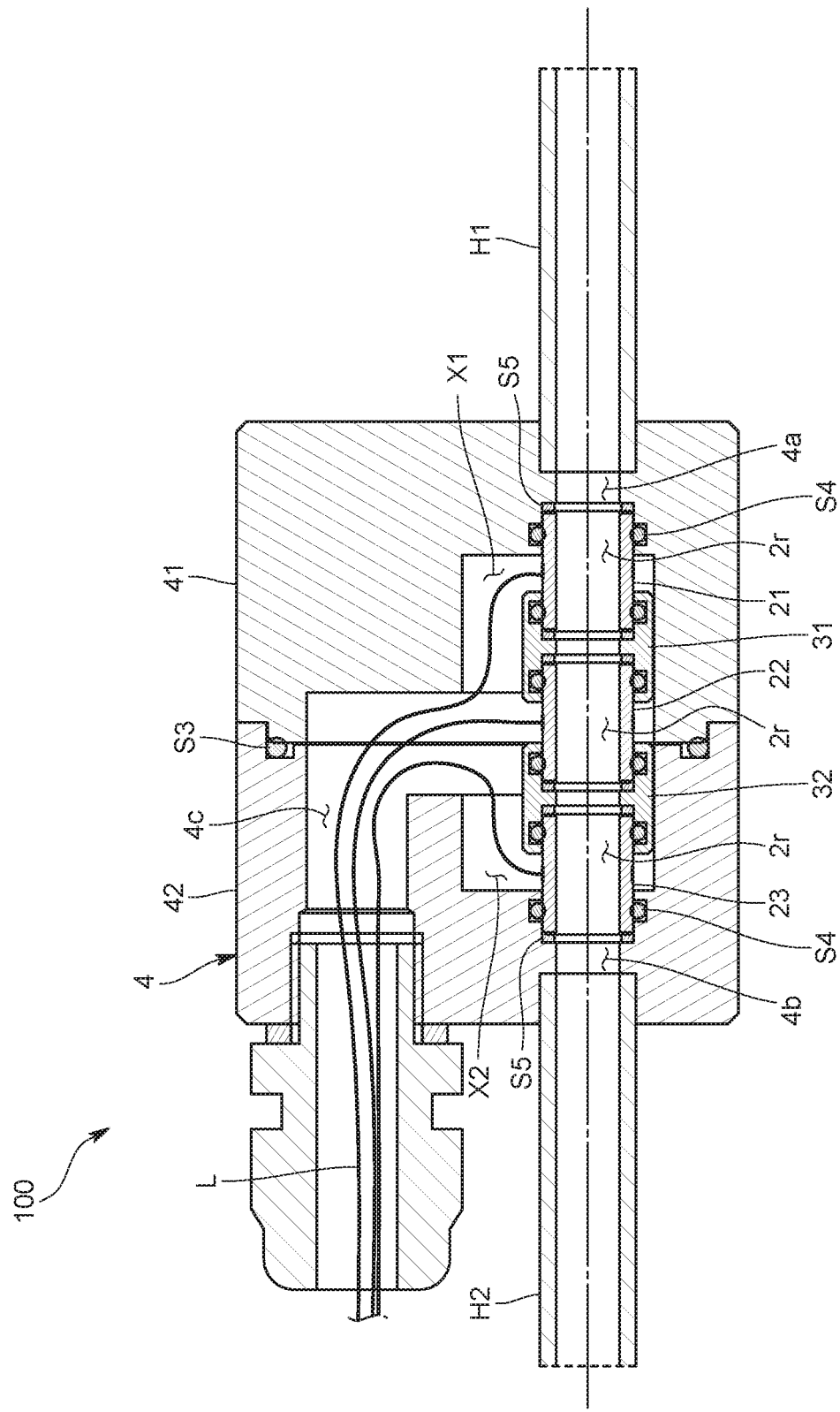
FIG. 1 is a cross-sectional schematic view showing a configuration of an electric conductivity meter of a first embodiment.

Concretely, the electric conductivity meter 100 comprises, as shown in FIG. 1, three cylindrical electrodes 21~23 inside of which formed are inner flow channels 2r where the liquid sample flows, two electrode holders 31, 32 that communicate the inner flow channels 2r of the three electrodes 21~23 with each other and that hold the three electrodes 21~23 and a housing block 4 that houses the three electrodes 21~23 and the two electrode holders 31, 32.

Each of the three electrodes 21~23 is made of a material having corrosion resistance to the liquid sample, for example, carbon such as glassy carbon or plastic formed carbon in this embodiment. In addition, the three electrodes 21~23 have the same shape. On a center part of an outer peripheral surface of each electrode 21~23 formed is an electrode pad part 2p made of, for example, nickel plating, to which a lead wire (L) is connected (refer to FIG. 2). The lead wire (L) is connected to an AC power supply (not shown in drawings) provided outside. A voltage with the same polarity is applied to the electrodes 21, 23 locating at both ends and a voltage with reverse polarity is applied to the electrode 22 locating in the center.

Each of the two electrode holders 31, 32 is made of a material having insulation, namely, fluorocarbon resin in this embodiment. In addition, the two electrode holders 31, 32 have the same shape.

The electrode holders 31, 32 hold the three electrodes 21~23 linearly so as to align the center axes of the electrodes 21~23 on the same axis. One of the electrode holders 31 holds the adjacent electrodes 21, 22 so as to align the center axes of the adjacent electrodes 21, 22, and the other electrode holder 32 holds the adjacent electrodes 22, 23 so as to align the center axes of the adjacent electrodes 22, 23.

Figure 2:
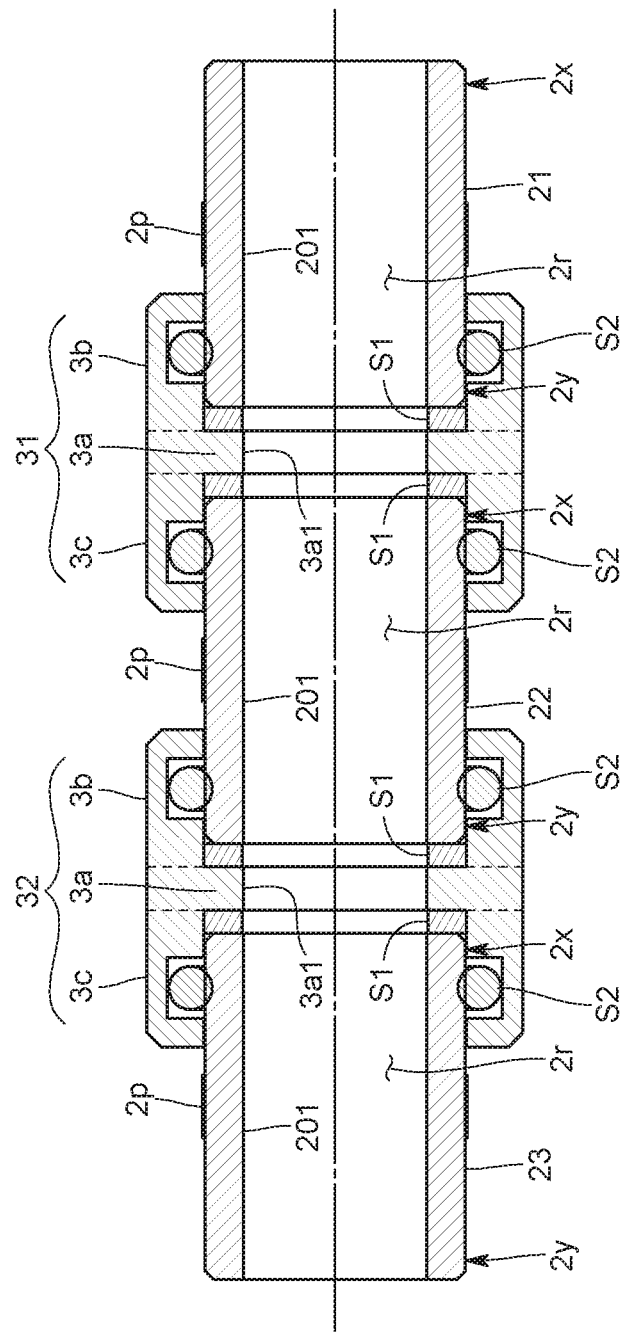
FIG. 2 is a cross-sectional view showing a relationship between two electrodes and an electrode holder of this embodiment.

Concretely, each of the electrode holders 31, 32 comprises, as shown in FIG. 2, a spacer part 3a locating between mutually facing axial direction end parts 2x, 2y of the two adjacent electrodes 21, 22 (22, 23) and two tubular parts 3b, 3c each of which surrounds peripheries of the mutually facing axial direction end parts 2x, 2y respectively. Each of the electrode holders 31, 32 in this embodiment is an integrally molded member in a shape of a rotating body.

The spacer part 3a is in an annular shape, and is arranged between the adjacent electrodes 21, 22 (22, 23) and specifies a distance between the adjacent electrodes 21, 22 (22, 23). The spacer part 3a is formed over the entire circumferential direction to face a whole circumference of the axial direction end surface of the mutually facing axial direction end parts 2x, 2y. In addition, an inner peripheral surface 3a1 (a flow channel side surface) of the spacer part 3a is so configured to be generally flat with an inner peripheral surface 201 (a flow channel side surface) of the electrodes 21~23 in a state that the electrode holders 31, 32 hold the electrodes 21~23. A circular seal member S1 such as packing is arranged between the axial direction end surface of the spacer part 3a and the axial direction end surface of each electrode 21~23. A gap in the flow channel direction between the adjacent two electrodes 21~23 is positioned through the spacer part 3a and the seal member S1. It is also preferable that the inner peripheral surface (the flow channel side surface) of the seal member S1 is generally flat with the inner peripheral surface 201 (the flow channel side surface) of the electrodes 21~23.

The cylindrical part 3b, 3c is of a cylindrical shape projecting from axial direction both end parts of the spacer part 3a toward axial direction outside. The cylindrical part 3b, 3c is so configured to cover a whole circumference of the outer surface of the axial direction end part 2x, 2y of the electrodes 21~23. In addition, two cylindrical parts 3b, 3c have generally the same shape and are so configured to locate each center axis of the cylindrical parts 3b, 3c on the same axis. A seal member S2 such as an O-ring is arranged between an inner surface of the cylindrical part 3b, 3c and the outer surface of the axial direction end surface of the electrode 21~23. The electrode holders 31, 32 and the electrodes 21~23 are positioned through the O-ring S2 so as to locate the center axis of the cylindrical part 3b, 3c and the center axis of the electrode 21~23 on the same axis.

Similar to the electrode holders 31, 32, the housing block 4 is made of a material having insulation and fluoro-resin in this embodiment.

The housing block 4 has, as shown in FIG. 1, an introducing path 4a whose cross-section is circle into which the liquid material is introduced and a discharging path 4b whose cross-section is circle from which the liquid material is discharged, and a lead wire space 4c to extend a lead wire (L) that is connected to the three electrodes 21~23 to outside. The housing block 4 in this embodiment is of generally a rectangular parallelepiped, however, it is not limited to this.

Concretely, the housing block 4 has a first block element 41 where the introducing path 4a is formed and a second block element 42 where the discharging path 4b is formed. A circular tube shaped outside introducing pipe (H1) is connected to the first block element 41 and the outside introducing pipe (H1) is in communication with the introducing path 4a. A circular tube shape outside introducing pipe (H2) is connected to the second block element 42 and the outside introducing pipe (H2) is in communication with the discharging path 4b.

Both of the first block element 41 and the second block element 42 have housing parts (X1), (X2) that house the electrode holders 31, 32 and the electrodes 21~23. The first block element 41 opens to a surface that faces the second block element 42, and is in communication with the introducing path 4a at an opposite side to the second block element 42. The second block element 42 opens to a surface that faces the first block element 41, and is in communication with the discharging path 4b at an opposite side to the first block element 41. A seal member (S3) such as an O-ring is arranged between a facing surface of the first block element 41 and a facing surface of the second block element 42. A concave part constituting a space 4c for lead wire is formed on a facing surface of the first block element 41 and a facing surface of the second block element 42 respectively.

The three electrodes 21~23 held by the electrode holders 31, 32 are housed in the housing part (X1), (X2). At this time the mutually facing axial direction end parts 2x, 2y of the electrodes 21, 23 locating at both sides are positioned liquid-tightly in the housing parts (X1), (X2) through seal members (S4) such as an O-ring or the like. In addition, a circular seal member (S5) such as packing is arranged between the mutually facing axial direction end parts 2x, 2y and the inner surfaces of the housing parts (X1), (X2). With this arrangement, inner flow channels 2r of the electrodes 21~23 are in communication with the introducing path 4a and the discharging path 4b.

Next, an example of assembling the electric conductivity meter 100 having the above-mentioned arrangement will be explained.

First, the lead wire (L) is connected to electrode pad parts 2p of each of the electrodes 21~23 by welding or the like. The electrodes 21~23 to which the lead wire (L) is connected are inserted into the cylindrical parts 3b, 3c of the electrode holders 31, 32 through the O-rings (S2). The packing (S1) is arranged between the spacer part 3a of the electrode holders 31, 32 and the axial direction end surface of the electrodes 21~23. With this procedure, a single electrode structure is assembled by holding three electrodes 21~23 with two electrode holders 31, 32.

This electrode structure is mounted on the housing part (X1) of one block element (for example, the first block element 41). At this time, the O-ring (S4) and the packing (S5) are interposed between the inner surface of the housing part (X1) and the electrode 21 of the electrode structure.

Next, the other block element (for example, the second block element 42) is fixed to the block element 41 by a fixing screw. When the two block elements 41, 42 are fixed each other by the fixing screw, the electrode structure is pushed in the flow channel direction by the two block elements 41, 42. At this time the O-ring (S3) is arranged between the facing surface of the first block element 41 and the facing surface of the second block element 42. The other end side of the electrode structure that is mounted on the housing part (X1) of the block element 41 is housed in the housing part (X2) of the other block element 42. At this time the O-ring (S4) and the packing (S5) are interposed between the inner surface of the housing part (X2) and the other electrode of the electrode structure.

Effect of the First Embodiment

In accordance with the electric conductivity meter 100 of this embodiment having the above arrangement, since the flow channel where the liquid sample flows is formed by the cylindrical three electrodes 21~23 and this arrangement is different from a conventional arrangement wherein electrodes project in a flow channel, the electrodes 21~23 hardly prevent the flow of the liquid sample. With this arrangement, even though the liquid sample is slurry, it is possible to reduce solid particles of the slurry that reside on the electrodes 21~23 and in the periphery of the electrodes 21~23.

In addition, since the distance between the electrodes 21~23 in the flow channel direction is specified by the spacer part 3a of the electrode holders 31, 32, and the center axis of each electrode 21~23 is positioned by the two cylindrical parts 3b, 3c, it is possible to improve the measurement accuracy.

Furthermore, since the two electrodes 21, 22 (22, 23) are held by the common electrode holder 31, 32, it is possible to facilitate an assemble property and reduce a number of components.

Second Embodiment

Next, a second embodiment of the electric conductivity meter in accordance with this invention will be explained with reference to drawings.

Similar to the first embodiment, the electric conductivity meter 100 in accordance with the second embodiment is used for measuring concentration of a fluid (hereinafter called as a liquid sample) such as silica-based or ceria-based slurry that is used for chemical mechanical polishing (CMP) in a semiconductor manufacturing process, and calculates electric conductivity of the liquid sample by measuring the electric conductivity of the liquid sample between at least two electrodes.

Figure 3:
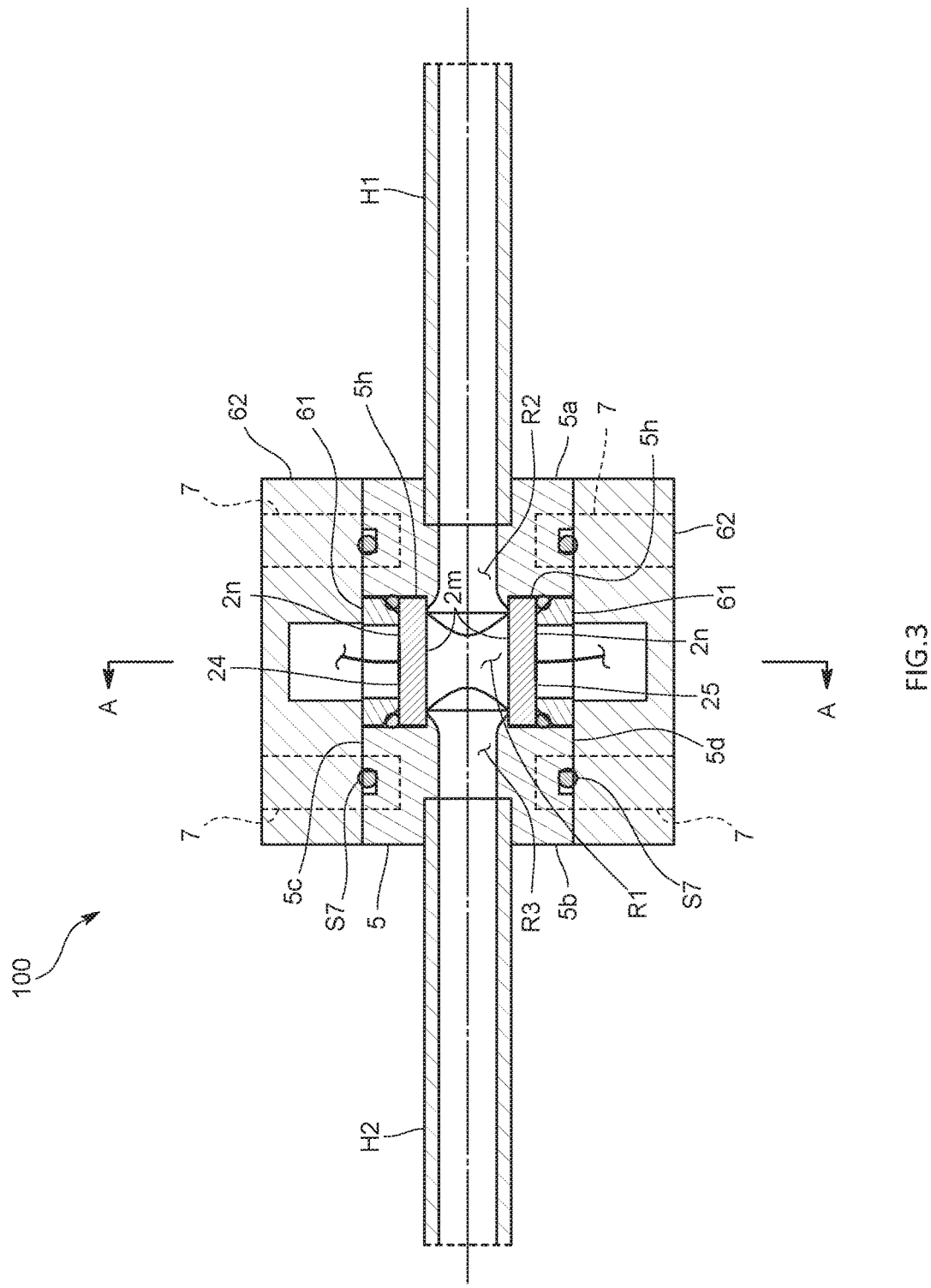
FIG. 3 is a cross-sectional schematic view showing a configuration of an electric conductivity meter of a second embodiment.
Figure 4:
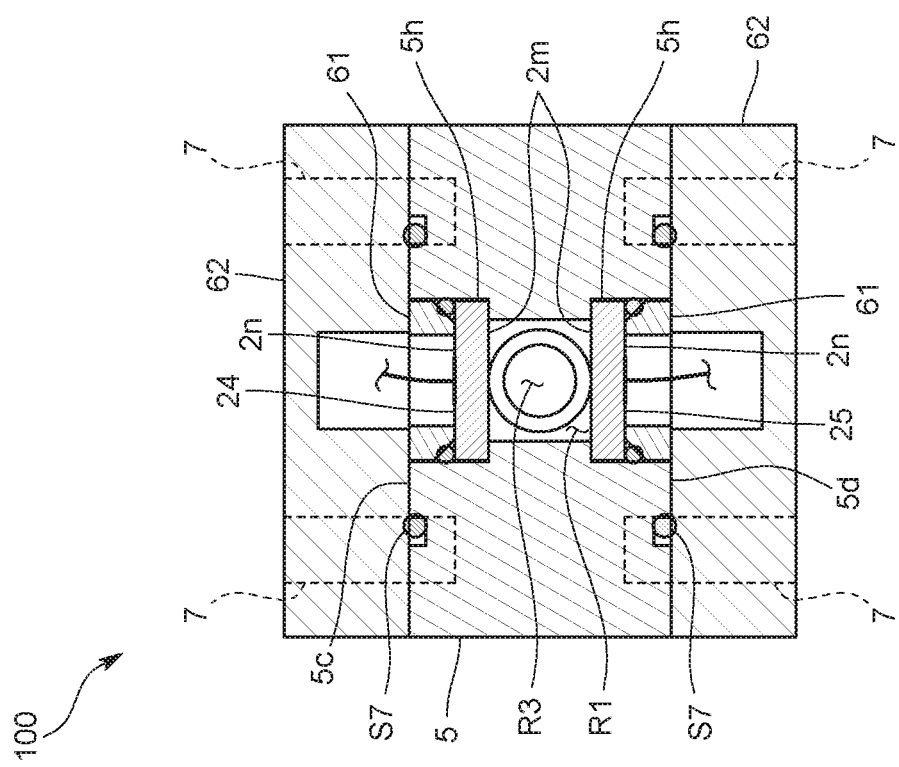
FIG. 4 is a cross-sectional view taken along a line A-A of this embodiment.
Figure 5:
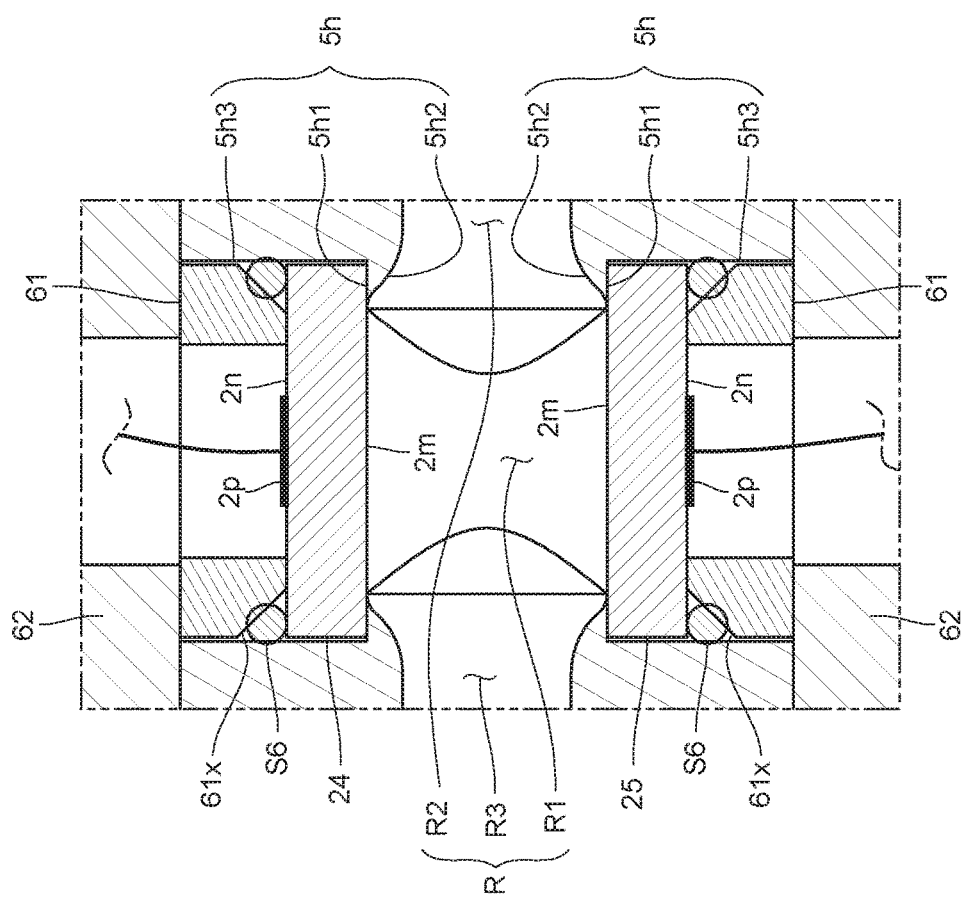
FIG. 5 is a partially enlarged cross-sectional view of a configuration near a through bore.

Concretely, the electric conductivity meter 100 comprises, as shown in FIG. 3~FIG. 5, a pair of electrodes 24, 25 and a flow channel block where a pair of the electrodes 24, 25 are provided and inside of which a flow channel (R) is formed.

Each of a pair of the electrodes 24, 25 is made of a material having corrosion resistance to the liquid sample, namely carbon such as glassy carbon or plastic formed carbon in this embodiment. In addition, each of a pair of the electrodes 24, 25 has the same shape, and is a plate-shaped circle from a plane view in this embodiment. One flat surface 2*m* of each electrode 24, 25 faces the flow channel side and the other flat surface 2*n* thereof faces opposite side. A center part of the other flat surface 2*n* formed is an electrode pad part 2*p* made of, for example, nickel plating and to which the lead wire (L) is connected. The lead wire (L) is connected to an AC power source (not shown in drawings) arranged outside.

The flow channel block 5 is generally of rectangular parallelepiped where the linear flow channel (R) is formed from one surface 5*a* to the other surface 5*b*. The flow channel (R) comprises a measurement space (R1) as being a space sandwiched between a pair of the electrodes 24, 25, an introducing path (R2) that introduces the liquid sample into the measurement space (R1) and a discharging path (R3) that discharges the liquid sample from the measurement space (R1).

Through bores 5*h* that are in communication with the measurement space (R1) in the flow channel and where the electrodes 24, 25 are arranged are formed on side surfaces 5*c*, 5*d* that face each other and that is along the flow channel direction of the flow channel block 5. One electrode 24 is arranged on the through bore 5*h* formed on one side surface 5*c* and the other electrode 25 is arranged on the through bore 5*h* formed on the other side surface 5*d*.

The through bores 5*h* are formed, especially as shown in FIG. 5, orthogonal to the flow channel direction, and an inner surface of the through bore 5*h* has an engaging part 5*h*1 with which a flow channel side end surface 2*m* of the electrodes 24, 25 engages, and an enlarging part 5*h*2 that enlarges as approaching the flow channel side at the flow channel side of the engaging part 5*h*1.

The inner surface of the through bore 5*h* has a big diameter part 5*h*3 facing an outer peripheral surface of the electrodes 24, 25, and the engaging part 5*h*1 that projects in a diameter direction inner side is formed on the lower end in the flow channel side of the big diameter part 5*h*3. The engaging part 5*h*1 is of a planer shape that makes contact with an outer edge part of the flow channel side end surface 2*m* of the electrodes 24, 25. The electrodes 24, 25 are fixed by making an engagement with step part comprising the big diameter part 5*h*3 and engaging part 5*h*1 formed inner surface of the through bore 5*h*.

In addition, the enlarging part 5*h*2 is of a tapered shape continuously formed on the engaging part 5*h*1, and is formed into a curved shape whose cross-section swells toward the flow channel direction in this embodiment. A cross-section of the enlarging part 5*h*2 is not limited to the curved shape swelling toward the flow channel direction, and may be a straight line shape.

The electrodes 24, 25 arranged on the through bore 5*h* are fixed by being pressed by a pressing member 62 toward the flow channel side through a spacer 61. A seal member (S6) such as an O-ring is arranged among the other flat surface 2*n* of the electrodes 24, 25, a tapered surface 61*x* of the spacer 61, and the big diameter part 5*h*3 of the through bore 5*h*.

Concretely, the pressing member 62 is pressed and fixed to the side surface 5*c*, 5*d* of the flow channel block 5 by a fastening mechanism 7 such as a fixing screw so that the electrodes 24, 25 are pressed against the engaging part 5*h*1 and fixed to the flow channel block 5. A seal member (S7) such as an O-ring is arranged between the flow channel block 5 and the pressing member 62.

Effect of the Second Embodiment

In accordance with this arrangement, since the inner surface of the through bore 5*h* where the electrodes 24, 25 are arranged has the enlarging part 5*h*2 that expands toward the flow channel side at the flow channel side of the engaging part 5*h*1 with which the electrodes 24, 25 engage in the flow channel side, it is possible to reduce space where the liquid sample resides as being space formed in front of the flow channel side end surface 2*m* of the electrodes 24, 25, and to hardly intercept smooth flow of the liquid sample. With this arrangement, even though the liquid sample is the slurry, it is possible to reduce solid particles of the slurry that reside on and around the electrodes 24, 25.

Third Embodiment

Next, a third embodiment of the electric conductivity meter in accordance with this invention will be explained with reference to drawings.

Figure 6:
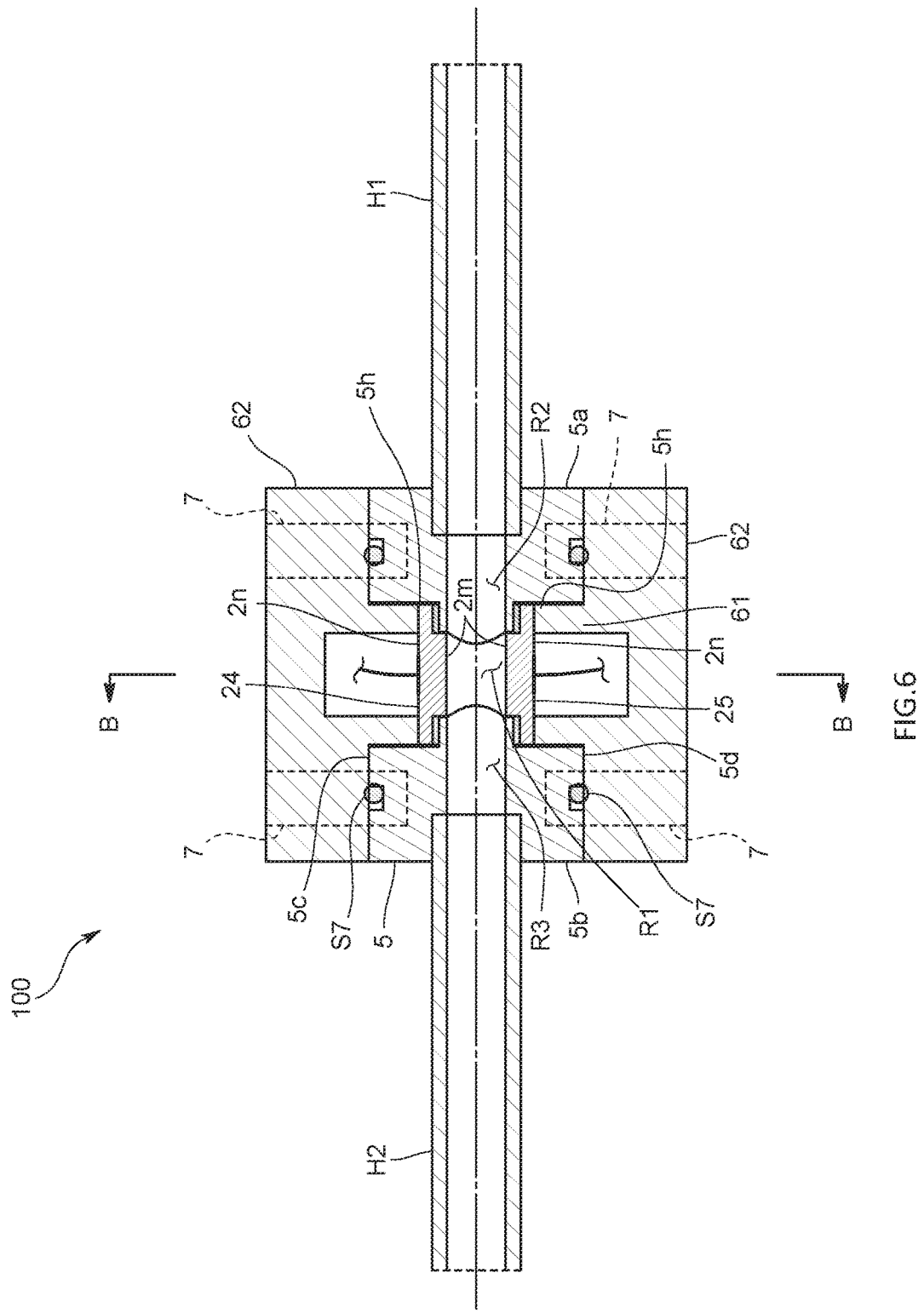
FIG. 6 is a cross-sectional schematic view showing a configuration of an electric conductivity meter of a third embodiment.
Figure 7:
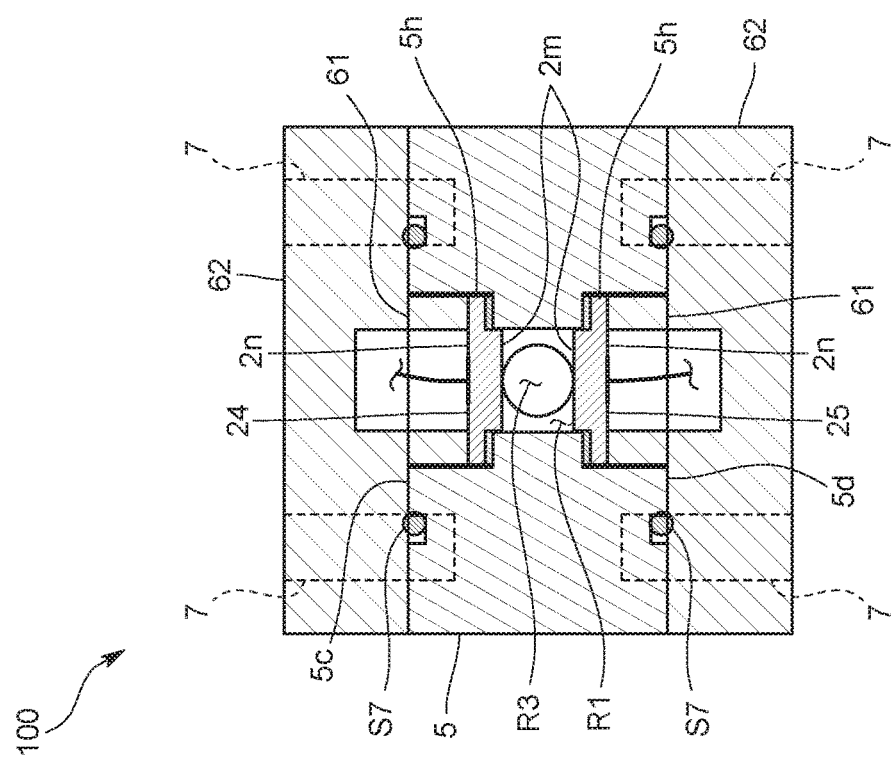
FIG. 7 is a cross-sectional view taken along a line B-B of this embodiment.

The electric conductivity meter 100 in accordance with the third embodiment has, as shown in FIG. 6~FIG. 8, a configuration of the through bore 5*h* of the flow channel block 5 and the electrodes 24, 25 different from those of the second embodiment. The same or corresponding components as those in the third embodiment are denoted by the same reference numerals as those in the second embodiment.

Concretely, the inner surface of the through bore 5*h* of the flow channel block 5 has, especially as shown in FIG. 8, the big diameter part 5*h*3 facing the outer peripheral surface of the electrodes 24, 25, and the engaging part 5*h*1 with which the flow channel side end surface 2*m* of the electrodes 24, 25 engages. The engaging part 5*h*1 is formed to project from the flow channel side bottom end of the big diameter part 5*h*3 toward the radial direction inner side. The engaging part 5*h*1 is a plate shaped facing the outer edge part of the flow channel side end surface 2*m* of the electrodes 24, 25. In addition, the flow channel side more than the engaging part 5*h*1 of the inner surface of the through bore 5*h* is a small diameter part 5*h*4 whose diameter is smaller than that of the big diameter part 5*h*3. The small diameter part 5*h*4 has the same cross-section in this embodiment. As mentioned above, the electrodes 24, 25 are engaged with and fixed to a step part that comprises the big diameter part 5*h*3 and the engaging part 5*h*1 and that is formed on the inner surface of the through bore 5*h*. In this embodiment, the pressing member 62 has the spacer 61.

Each of the electrodes 24, 25 has a projecting part 2*t* that projects toward the flow channel side more than the engaging part 5*h*1 of the through bore 5*h*. The projecting part 2*t* has a diameter that is generally the same as that of the small diameter part 5*h*4 of the through bore 5*h*, and has an outer diameter that fits into the small diameter part 5*h*4 in this embodiment. In addition, the projecting part 2*t* is so configured that the distal end surface 2*t*1 of the projecting part 2*t* locates on generally the same surface as that of a part of the inner surface of the flow channel (R). To locate on generally the same surface means that the distal end surface 2*t*1 of the projecting part 2*t* locates on the same surface as that of a part of the inner surface of the flow channel (R) to an extent that no solid particle resides or to an extent that the measurement error can be ignored even though the solid particles reside.

Effect of Third Embodiment

In accordance with this arrangement, since the inner surface of the through bore 5*h* where the electrodes 24, 25 are arranged has the engaging part 5*h*1 with which the electrodes 24, 25 make an engagement and the electrodes 24, 25 have the projecting part 2*t* that projects toward the flow channel side more than the engaging part 5*h*1, it is possible to reduce space where the liquid sample resides as being space formed in front of the flow channel side end surface 2*m* of the electrodes 24, 25, and to hardly intercept smooth flow of the liquid sample. With this arrangement, even though the liquid sample is the slurry, it is possible to reduce solid particles of the slurry that reside on and around the electrode 24, 25.

Other Embodiment

The present claimed invention is not limited to each of the above-mentioned embodiments.

In the first embodiment, the electric conductivity meter 100 uses three electrodes, however, two electrodes may be used. In this case, the electric conductivity meter holds two electrodes by one electrode holder.

In addition, the electrode in the first embodiment is cylindrical in shape, however, the shape may be tube.

The electrode in the second and third embodiments is circle from a plane view, however, it may be other shape such as rectangle from a plane view.

A pair of the electrodes in the second and third embodiments are arranged to sandwich the flow channel, however, they may be arranged side by side along the flow channel.

The expanding part in the second embodiment is tapered, however, it may be any as far as a gap between the introducing path and the flow channel side end surface and a gap between the discharging path and the flow channel side end surface are smoothly connected.

The slurry in each of the embodiments is silica-based or ceria-based, however, it may be other-based.

The electric conductivity meter in the above-mentioned embodiments calculates the electric conductivity ratio (S/m (Siemens/meter)) of the liquid sample by measuring the electric conductivity of the liquid sample, however, it may calculate electric conductivity (S/cm (Siemens/centimeter)), or may calculate specific electrical resistance (Ω·m) or resistance (Ω).

In addition, the present claimed invention is not limited to the above-mentioned embodiment, and it is a matter of course that the present claimed invention may be variously modified without departing from a spirit of the invention.

EXPLANATION OF CODE

100 . . . electric conductivity meter
21, 22, 23 . . . electrode
2*r* . . . inner flow channel
201 . . . flow channel side surface of electrode
31, 32 . . . electrode holder
3*a* . . . spacer part
3*h*, 3*c* . . . tubular part
3*a*1 . . . flow channel side surface of spacer part
4 . . . housing block
4*a* . . . introducing path
4*b* . . . discharging path
24, 25 . . . electrode
2*m* . . . flow channel side end surface of electrode
2*t* . . . projecting part
5 . . . flow channel block
5*h* . . . through bore
5*h*1 . . . engaging part
5*h*2 . . . enlarging part

The invention claimed is:

1. An electric conductivity meter that measures electric conductivity of a fluid, wherein comprising
at least two tubular electrodes inside of each of which respectively formed is an inner flow channel where the fluid flows, and
an electrode holder that communicates each of the inner flow channels of the above-mentioned at least two electrodes and that holds the above-mentioned at least two electrodes, and is characterized by that
the electrode holder holds the above-mentioned at least two electrodes by making an engagement with each outer peripheral surface of mutually facing axial direction end parts of the above-mentioned at least two electrodes.

2. The electric conductivity meter described in claim 1, wherein
the electrode holder comprises a spacer part that locates between the mutually facing axial direction end parts and two tubular parts each of which surrounds each of the outer peripheral surfaces of the mutually facing axial direction end parts.

3. The electric conductivity meter described in claim 2,
the spacer part is formed over the entire circumferential direction of the mutually facing axial direction end parts, and
an inner peripheral surface of the spacer part and an inner peripheral surface of the electrodes locate on approximately the same plane.

4. The electric conductivity meter described in claim 1,
the above-mentioned at least two electrodes are made of carbon.

5. The electric conductivity meter described in claim 1, further comprising
a housing block that houses the above-mentioned at least two electrodes and the electrode holder and that has an introducing path to introduce the fluid and a discharging path to discharge the fluid.

6. The electric conductivity meter described in claim 5,
the electrode holder is positioned to the housing block, and the inner flow channel communicates with the introducing path and the discharging path.

7. An electric conductivity meter that has an electrode arranged to make contact with a fluid flowing in a flow channel, wherein comprising
a flow channel block inside of which formed is the flow channel, and is characterized by that
the flow channel block has a through bore that is in communication with the flow channel and where the electrode is arranged, and
an inner surface of the through bore has an engaging part with which the flow channel side end surface of the electrode makes an engagement and an expanding part that expands toward the flow channel side at the flow channel side of the engaging part.

8. An electric conductivity meter that has an electrode arranged to make contact with a fluid flowing in a flow channel, wherein comprising
   a flow channel block inside of which formed is the flow channel, and is characterized by that
   the flow channel block has a through bore that is in communication with the flow channel and where the electrode is arranged,
   an inner surface of the through bore has an engaging part with which the flow channel side end surface of the electrode makes an engagement, and
   the electrode has a projecting part that projects to the flow channel side more than the engaging part.

* * * * *